(12) United States Patent
Takeuchi et al.

(10) Patent No.: US 9,808,166 B2
(45) Date of Patent: Nov. 7, 2017

(54) PULSE PHOTOMETRY PROBE

(75) Inventors: Masahiro Takeuchi, Tokyo (JP);
Noriaki Todokoro, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 553 days.

(21) Appl. No.: 12/491,211

(22) Filed: Jun. 24, 2009

(65) Prior Publication Data
US 2009/0318819 A1    Dec. 24, 2009

(30) Foreign Application Priority Data
Jun. 24, 2008   (JP) .................................. 2008-164392

(51) Int. Cl.
| | |
|---|---|
| A61B 5/026 | (2006.01) |
| A61B 5/1455 | (2006.01) |
| A61B 5/00 | (2006.01) |
| A61B 5/024 | (2006.01) |

(52) U.S. Cl.
CPC .......... *A61B 5/0261* (2013.01); *A61B 5/0059* (2013.01); *A61B 5/02444* (2013.01); *A61B 5/14552* (2013.01); *A61B 5/6826* (2013.01); *A61B 5/6829* (2013.01); *A61B 5/6838* (2013.01); *A61B 2562/164* (2013.01)

(58) Field of Classification Search
CPC . A61B 5/0059; A61B 5/02444; A61B 5/6829; A61B 5/6838; A61B 5/6826; A61B 2562/164; A61B 5/0261; A61B 5/1455
USPC ......................................... 600/481, 500–503
See application file for complete search history.

(56) References Cited

U.S. PATENT DOCUMENTS

| | | | | |
|---|---|---|---|---|
| 4,865,038 A | * | 9/1989 | Rich et al. .................... | 600/344 |
| 5,680,857 A | * | 10/1997 | Pelikan .............. | A61B 5/02427 |
| | | | | 600/323 |
| 5,830,136 A | * | 11/1998 | Delonzor et al. ............. | 600/323 |
| 6,112,107 A | * | 8/2000 | Hannula ............ | A61B 5/14552 |
| | | | | 600/310 |
| 6,622,034 B1 | * | 9/2003 | Gorski et al. .................. | 600/344 |
| 6,694,160 B2 | * | 2/2004 | Chin ............................. | 600/344 |

(Continued)

FOREIGN PATENT DOCUMENTS

| | | | |
|---|---|---|---|
| JP | 2003-225215 A | 8/2003 | |
| JP | 2004-049579 A | 2/2004 | |
| WO | WO 2009-014419 | * 9/2009 | ............... A61B 5/00 |

OTHER PUBLICATIONS

"Applying Perforations." Digital Print Project. Apr. 22, 2008.*
"Slit." Oxford Dictionaries Online.*
"Score." Oxford Dictionaries Online.*

*Primary Examiner* — Meredith Weare
(74) *Attorney, Agent, or Firm* — Kenealy Vaidya LLP

(57) ABSTRACT

A pulse photometry probe includes: a light emitter having a first face from which light is emitted toward a living body; a light receiver having a second face which receives the light from the living body; a surface sheet which faces the first face of the light emitter and the second face of the light receiver; a cover sheet in which at least one slit is formed; and a lead wire which includes: a first lead wire connected to one of the light emitter and the light receiver; a second lead wire connected to the other one of the light emitter and the light receiver; and a basal portion at which the first lead wire and the second lead wire are bundled. The second lead wire includes at least one slack portion between the basal portion and the other one of the light emitter and the light receiver.

18 Claims, 8 Drawing Sheets

(56) References Cited

U.S. PATENT DOCUMENTS

| | | |
|---|---|---|
| 6,763,255 B2 * | 7/2004 | DeLonzor et al. ............ 600/323 |
| 7,561,905 B2 * | 7/2009 | Delonzor et al. ............. 600/310 |
| 2002/0038082 A1 * | 3/2002 | Chin ............................ 600/323 |
| 2002/0072681 A1 * | 6/2002 | Schnali ........................ 600/507 |
| 2002/0173708 A1 * | 11/2002 | DeLonzor et al. ........... 600/323 |
| 2003/0100840 A1 * | 5/2003 | Sugiura et al. ............... 600/504 |
| 2005/0197550 A1 * | 9/2005 | Al-Ali et al. ................. 600/323 |
| 2006/0258922 A1 * | 11/2006 | Mason et al. ................. 600/323 |
| 2010/0317945 A1 * | 12/2010 | Schraa et al. ................. 600/324 |

\* cited by examiner

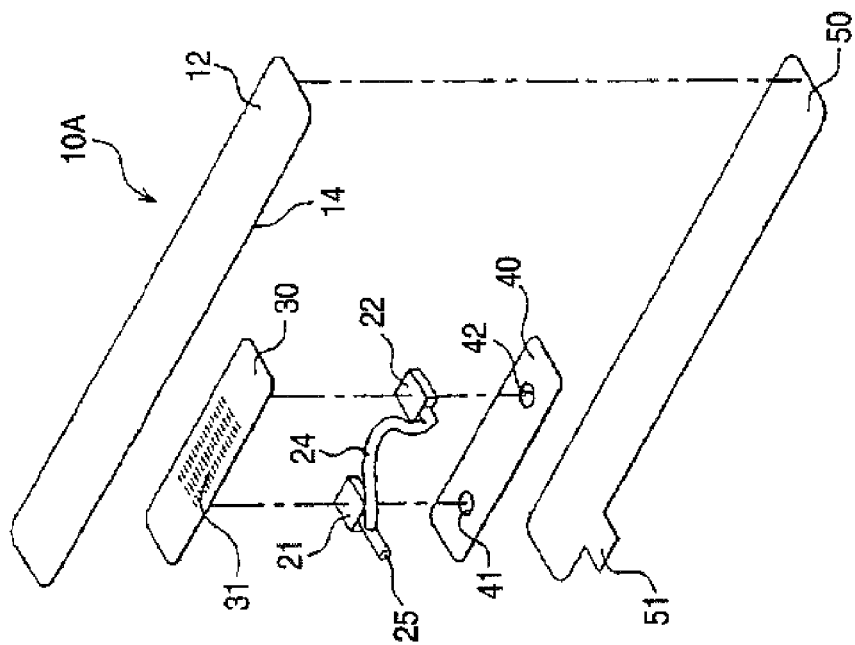
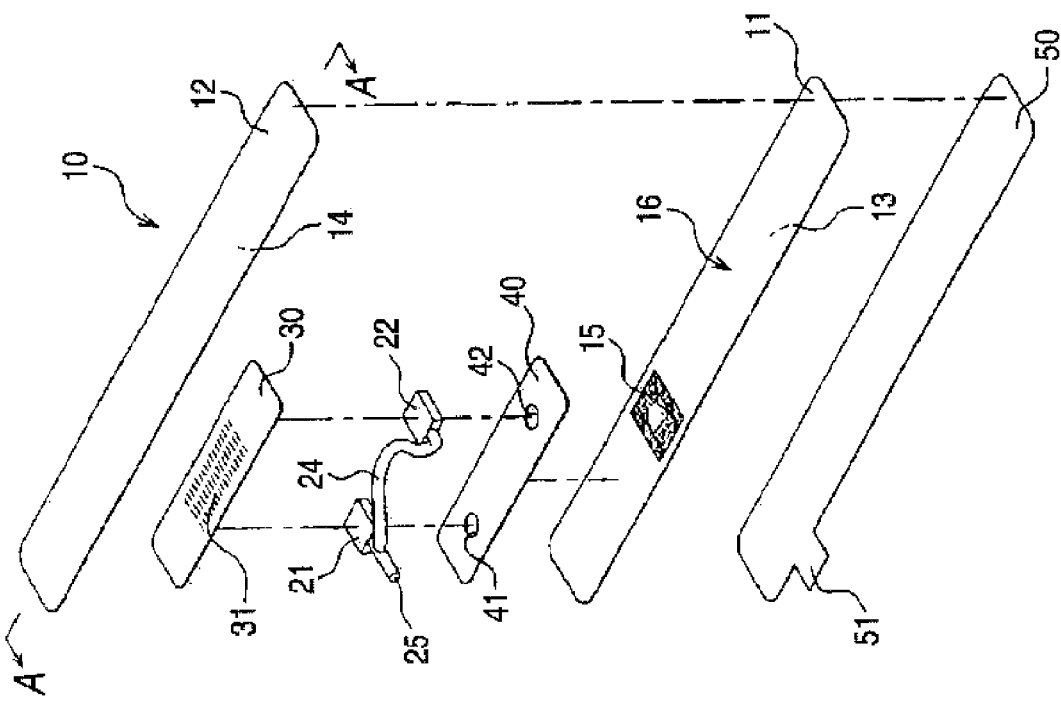

PULSE PHOTOMETRY PROBE

BACKGROUND OF THE INVENTION

The present invention relates to a pulse photometry probe for measuring a pulse wave and a light absorption material in blood by the pulse photometry method.

In a related-art probe of this type, a light emitter and a light receiver are disposed in a long attaching member and a sensor holding member so as to be opposed to each other in a state where the probe is attached to a living body. In a use state, the sensor holding member is attached to a living body such as a finger while the sensor holding member is bent and then wound around the living body (see FIGS. 1 and 2 of JP-A-2004-49579 and FIG. 4 of JP-A-2003-225215).

In such a probe, however, the sensor holding member, the attaching member, and the like must protect the light emitter and the light receiver, and therefore have a certain degree of rigidity. Consequently, the probe is difficult to be properly fitted to the living body, so that apertures between the probe and the living body such as shown in FIGS. 6A to 6C may be sometimes formed. When disturbance light enters through the apertures and is detected by the light receiver, a false measurement may be caused.

Furthermore, cords which are placed in the sensor holding member, the attaching member, and the like have a certain degree of rigidity. Similarly with the sensor holding member and the attaching member, the cords hinder the probe from being properly fitted to a living body. In a configuration where a cable extends in a direction which is substantially perpendicular to a narrow-width edge of the probe and two lead wires in the cable are separated in a basal portion to be connected respectively to the light emitter and the light receiver, for example, the lead wires are disposed so as to extend to elements which are remote from the basal portion, without being substantially bent. In the case where the sensor is attached to a living body such as a finger, therefore, deformation in which the probe is formed into a shape fitted to the living body is hindered.

SUMMARY

It is therefore an object of the invention to provide a pulse photometry probe in which, when attached to a living body, is properly fitted to the living body, disturbance light is suppressed from entering, and a biological signal can be adequately measured.

In order to achieve the object, according to the invention, there is provided a pulse photometry probe comprising:
 a light emitter having a first face from which light is emitted toward a living body;
 a light receiver having a second face which receives the light from the living body;
 a surface sheet which faces the first face of the light emitter and the second face of the light receiver;
 a cover sheet in which at least one slit is formed, the light emitter and the light receiver which are disposed between the surface sheet and the cover sheet; and
 a lead wire which includes:
  a first lead wire connected to one of the light emitter and the light receiver;
  a second lead wire connected to the other one of the light emitter and the light receiver; and
  a basal portion at which the first lead wire and the second lead wire are bundled,
 wherein the second lead wire includes at least one slack portion between the basal portion and the other one of the light emitter and the light receiver.

The pulse photometry probe may further include a first sheet which covers the surface sheet and the cover sheet.

The slit may pass through the cover sheet.

The slit may have a bottom portion on the cover sheet without passing through the cover sheet.

The basal portion may be covered by at least one of the cover sheet and the first sheet.

The second lead wire may extend toward the other one of the light emitter and the light receiver at an angle, which is 30 degrees or more, from the basal portion, with respect to a direction in which the light emitter and the light receiver are arranged.

A light intensity adjuster may be disposed in a portion of the surface sheet. The portion of the surface sheet may face the second face of the light receiver.

The pulse photometry probe may further include a second sheet to be in contact with the living body. The surface sheet may include a third face which faces the light emitter and the light receiver and a fourth face opposite to the third face. The second sheet may face the fourth face of the surface sheet.

A light intensity adjuster may be disposed in a portion of the second sheet. The portion of the second sheet may face the second face of the light receiver.

The slit may enable the cover sheet to be elastic in a direction in which the light emitter and the light receiver are arranged.

The cover sheet may protect the light emitter and the light receiver.

The slack portion may attain an adequate length of the second lead wire, when the pulse photometry probe is attached to the living body.

The slit may extend in a direction perpendicular to a longitudinal direction of the cover sheet.

The slit may be disposed between a first portion of the cover sheet facing the light emitter and a second portion of the cover sheet facing the light receiver.

A plurality of the slits may be formed in the cover sheet.

The slack portion may have a shape including at least one bent portion.

BRIEF DESCRIPTION OF THE DRAWINGS

FIGS. 1A and 1B are assembly perspective views of an embodiment of a pulse photometry probe of the present invention.

DETAILED DESCRIPTION OF EMBODIMENTS

Figure 2:
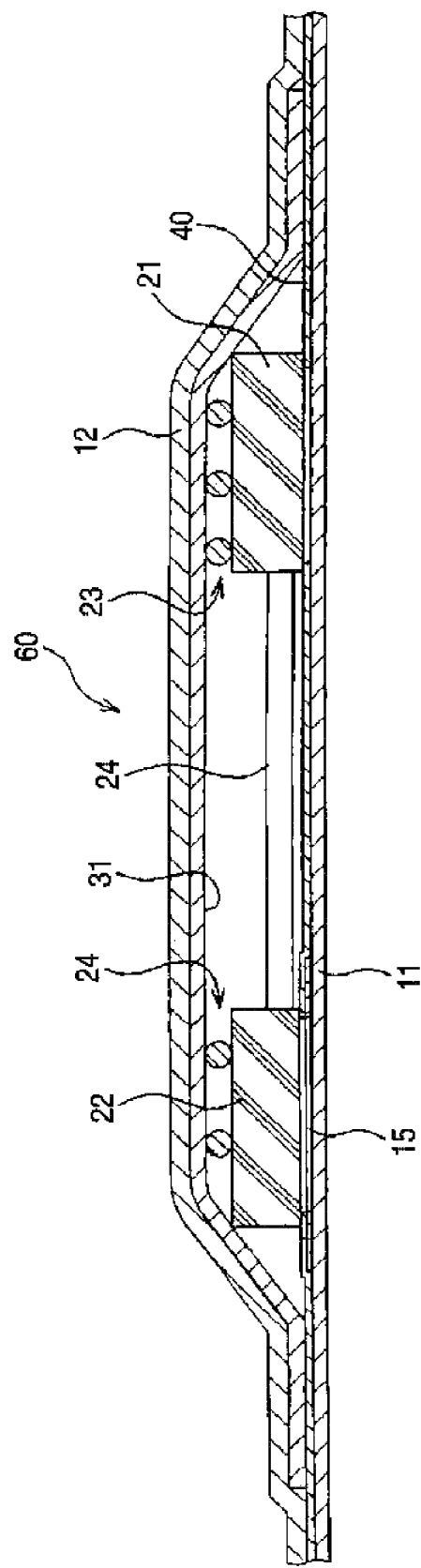
FIG. 2 is a section view of the assembled pulse photometry probe, taken along A-A in FIG. 1A.

Hereinafter, an embodiment of the pulse photometry probe of the invention will be described with reference to the accompanying drawings. In the figures, the identical components are denoted by the same reference numerals, and duplicated description is omitted. As shown in FIG. 1A, a pulse photometry probe 10 of the embodiment includes a light emitter 21, a light receiver 22, a second sheet 11, a first sheet 12, a cover sheet 30, and a surface sheet 40. FIG. 2 is a section view taken along A-A in a state where the pulse photometry probe is completely assembled.

The second sheet 11 is a long sheet which is configured by, for example, nonwoven fabric, which is located on a light-emitting side face of the light emitter 21 and on a light-receiving side face of the light receiver 22, and which is to be in contact with living tissue. A living-body contact face 13 is formed as an adhesive resin layer. In a state where the pulse photometry probe has not been used, a peel off sheet 50 having a gripper 51 which is to be used as a tab in a peeling operation is bonded to the living-body contact face 13. The area of the peel off sheet 50 other than the gripper 51 is equal to that of the second sheet 11.

Also the first sheet 12 is long and configured by, for example, nonwoven fabric. The first sheet 12 is disposed at a position where the first sheet 12 is opposed to the second sheet 11 through the light emitter 21 and the light receiver 22. The surface of the first sheet 12 which is opposed to the light emitter 21 and the light receiver 22 is formed as an adhesive resin layer surface 14.

The surface sheet 40 is a sheet which is in contact with the light-emitting side face of the light emitter 21 and the light-receiving side face of the light receiver 22, and which functions as a cover for them. For example, the surface sheet may be configured by a resin sheet in which an adhesive resin layer is formed on the both surfaces. In the surface sheet 40, a hole 41 through which light emitted from the light emitter 21 can pass is formed, and another hole 42 through which light emitted from the light emitter 21 and entering through living tissue to which the probe is attached can pass is formed.

Figure 3A:
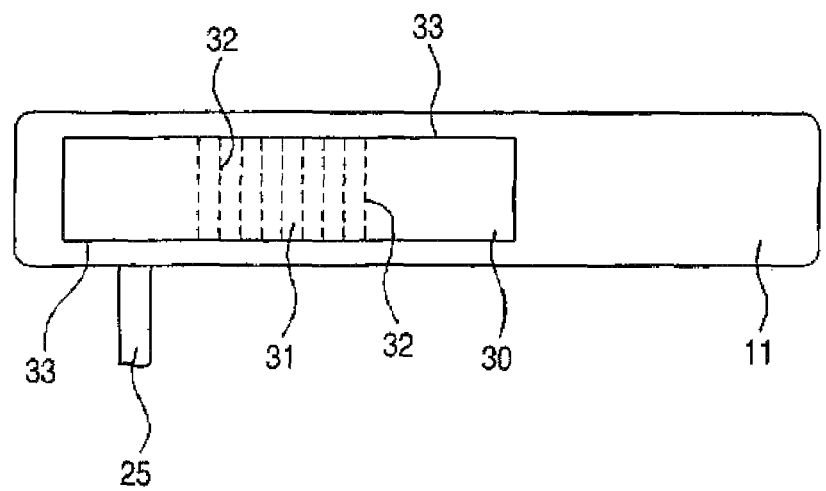
FIGS. 3A and 3B are plan views showing a state where a cover sheet is exposed in the embodiment of the pulse photometry probe.
Figure 3B:
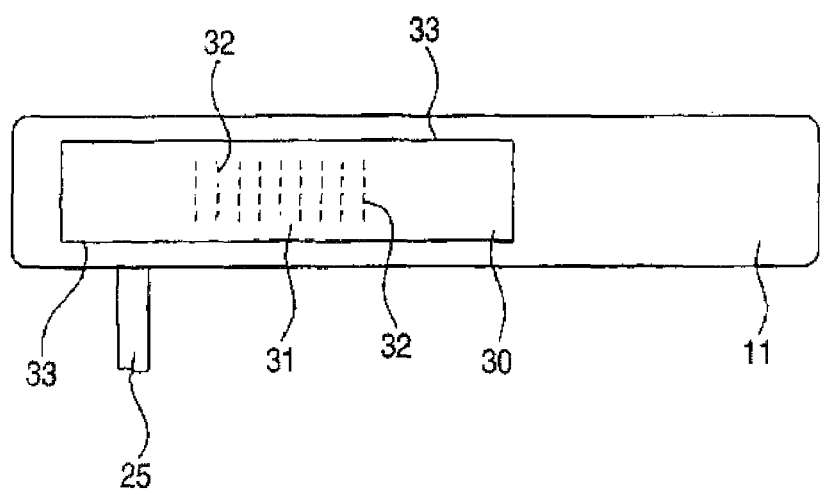

The cover sheet 30 is sandwiched by the first sheet 12, and the light emitter 21 and the light receiver 22, and the cover sheet 30 protects the light emitter 21 and the light receiver 22. For example, the cover sheet 30 is configured by a resin sheet which is slightly thicker than the surface sheet 40, and adhesive resin layers are formed on the both faces of the cover sheet 30. Alternatively, the cover sheet 30 may be configured by a sheet in which two kinds of sheets having adhesive resin layers on the both faces are stacked. One of the two kinds of sheets may be configured by nonwoven fabric having adhesive resin layers on the both faces. In the cover sheet 30, slits 31 are formed in a portion between positions where the light emitter 21 and the light receiver 22 are respectively located. The slits 31 are formed by incision lines 32 arranged in a direction along which the cover sheet 30 can be elastic in the distance direction of the light emitter 21 and the light receiver 22 (in the direction in which the light emitter 21 and the light receiver 22 are arranged). In the embodiment, as shown in FIG. 3A, the incision lines 32 extend in a direction which is perpendicular to a long side 33 of the cover sheet 30 (a longitudinal direction of the cover sheet 30). As shown in FIG. 3B, each of the incision lines 32 may have a length which is about 60% of a short side 35 of the cover sheet 30. The slits 31 are formed in a full-penetration state in which the slits 31 are fully penetratingly cut into the cover sheet 30 (the slits 31 pass through the cover sheet 30), or in a half-penetration state in which the slits 31 are halfway penetratingly cut into or do not penetrate through the cover sheet 30 (the slits have bottom portions on the cover sheet 30 without passing through the cover sheet 30).

The light emitter 21 emits light toward living tissue in a state where the pulse photometry probe 10 is attached to a living body, and is configured so as to include an LED. The light receiver 22 receives the light which is emitted from the light emitter 21, and which reaches the light receiver 32 through the living tissue, and is configured so as to include a light receiving element.

A lead wire 23 (first lead wire) is connected to the light emitter 21 so that an electric power is supplied to the light emitter. Another lead wire 24 (second lead wire) is connected to the light receiver 22 so that a signal obtained by receiving the light which is emitted from the light emitter 21, and which reaches the light receiver 22 through the living tissue, and then performing photoelectrical conversion can be taken out. The lead wire 23 and the lead wire 24 are bundled into one lead wire 25, for example, in the vicinity of the light emitter 21.

Figure 4:
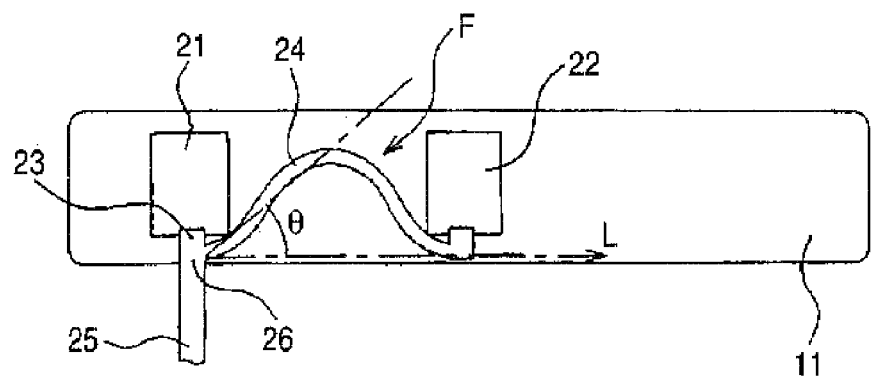
FIG. 4 is a plan view showing a state where a second lead wire having a slack portion is exposed in the embodiment of the pulse photometry probe.

The portion where the lead wires 23 and 24 are bundled into the one lead wire 25 is referred to as the basal portion 26. The second lead wire 24 has a slack portion F which attains an adequate length extending from the basal portion 26 to the light receiver 22. In other words, as shown in FIG. 4, the second lead wire 24 extends toward the light receiver 22 at an angle θ which is 30 degrees or more from the basal portion 26, with respect to the distance direction L of the light emitter 21 and the light receiver 22.

In the second sheet 11, a light intensity adjuster 15 is disposed in a region corresponding to (facing) the light-receiving side face of the surface sheet 40. The light intensity adjuster 15 is formed by printing (such as silk-screen printing) in, for example, blue on the inner side face 16 which is the face opposite to the living-body contact face 13. In the light intensity adjuster 15, at a position corresponding to the hole 42 of the surface sheet 40, the printing is not performed in a range having the same shape as the hole 42.

FIG. 1B shows a pulse photometry probe 10A having a configuration which does not include the second sheet 11. In the pulse photometry probe 10A, the rear face side of the surface sheet 40 in the state of FIG. 1B is formed as an adhesive resin layer. The adhesive resin layer and a part of the adhesive resin layer surface 14 of the first sheet 12 have a function of contacting with living tissue. Also the light intensity adjuster 15 is not included in the pulse photometry probe 10A. However, a light intensity adjuster may be disposed in a portion (region) of the surface sheet 40 corresponding to (facing) the light-receiving side face of the light receiver 22.

Figure 5:
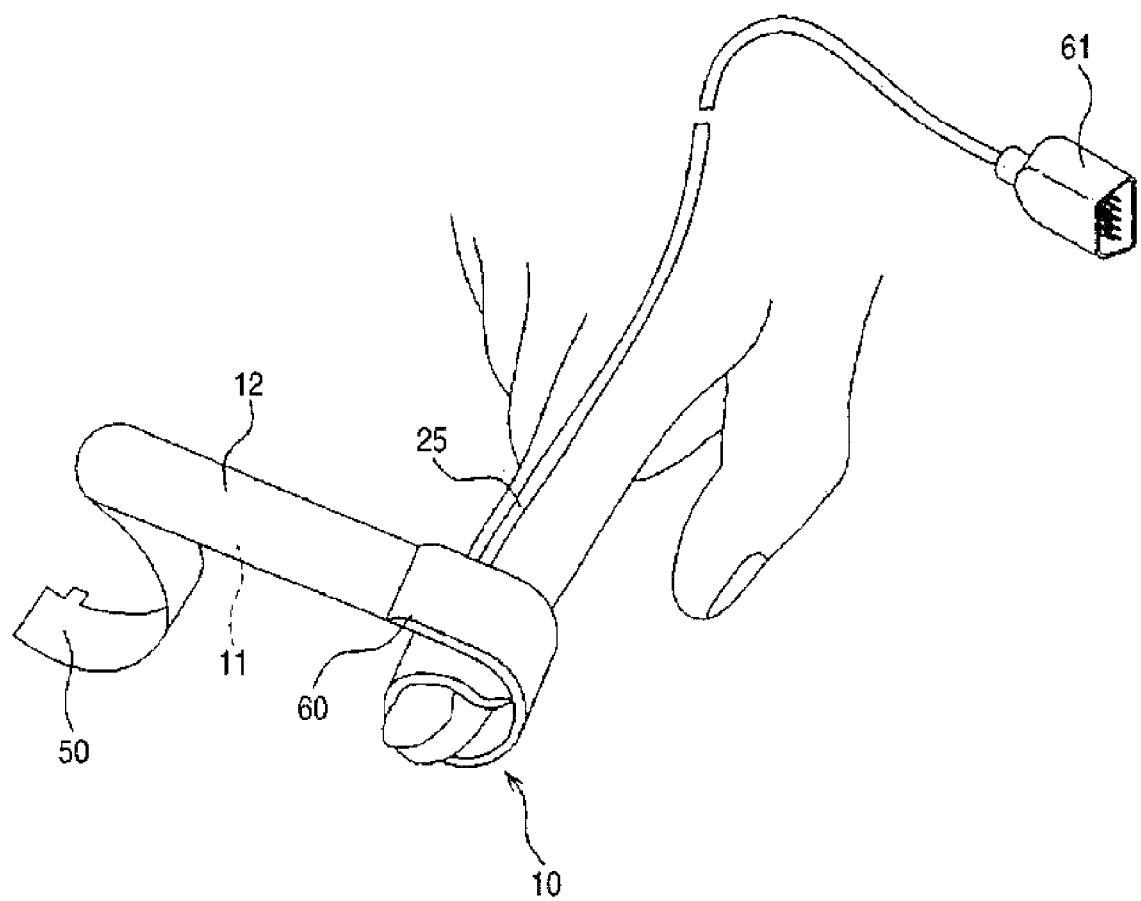
FIG. 5 is a perspective view showing a state where the embodiment of the pulse photometry probe is attached to a finger.

The light emitter 21 and the light receiver 22 are located and overlapped with each other at an adequate position with respect to the cover sheet 30 and the surface sheet 40, and fixed so as not to be positionally displaced, by the adhesive agent of the cover sheet or that of the surface sheet. A measuring portion 60 which includes the light emitter 21, the light receiver 22, the cover sheet 30, and the surface sheet 40 that are fixed are located and stacked at a predetermined position between the second sheet 11 and the first sheet 12, and fixed so as not to be positionally displaced, by the adhesive agent of the cover sheet 30 or that of the surface sheet 40. As shown in FIG. 5, the measuring portion 60 is slightly thicker than the other portion.

The thus configured pulse photometry probe 10 is used in the following manner. As shown in FIG. 5, the peel off sheet 50 is peeled off, the second sheet 11 is bonded so that the light-emitting side face of the light emitter 21 is located in the vicinity of the nail line of a finger, and the measuring portion 60 is wound around the finger. Alternatively, depending on a subject, the measuring portion 60 may be wound around a part of the subject such as the dorsum or toe of a foot. At this time, the light-receiving side face of the light receiver 22 is bonded to a position where the surface is opposed to the light-emitting side face of the light emitter 21 through the finger. Furthermore, the second sheet 11 in the portion where the measuring portion 60 of the pulse photometry probe 10 does not exist is bonded, thereby completing the preparation for the measurement.

A connector 61 shown in FIG. 5 is disposed in one end of the lead wire 25. The connector 61 is connected to a measurement apparatus which measures a pulse wave or a light absorption material in blood by the pulse photometry method, and then a necessary measurement is performed.

Figure 6A:
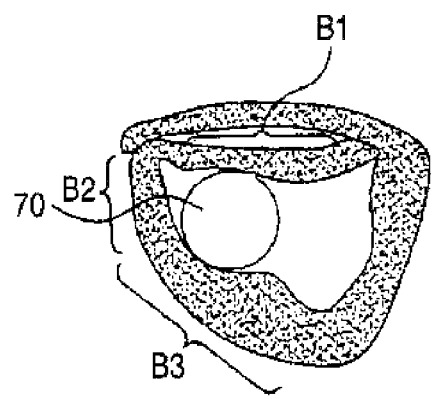
FIGS. 6A to 6C are plan views of a state where a related-art pulse photometry probe is wound around three kinds of bars having different diameters.
Figure 6B:
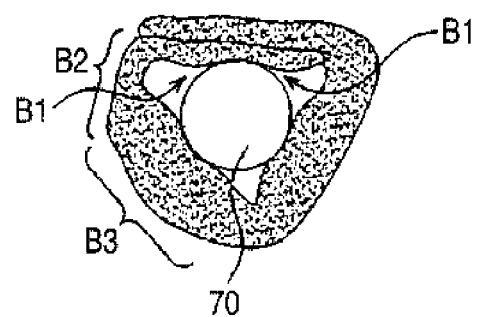
Figure 6C:
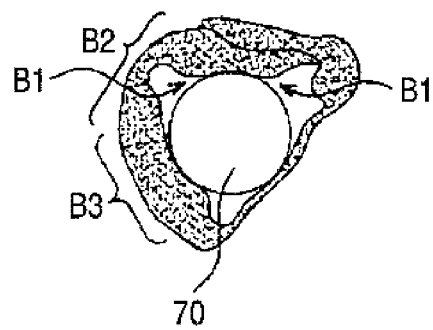
Figure 7A:
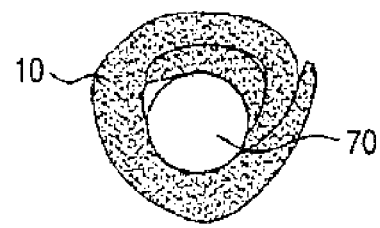
FIGS. 7A to 7C are plan views of a state where the pulse photometry probe of the invention is wound around three kinds of bars having different diameters.
Figure 7B:
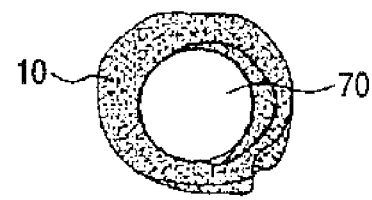
Figure 7C:
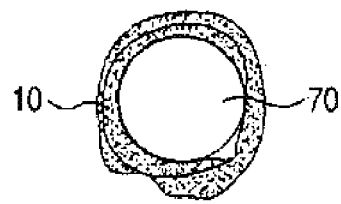

FIGS. 6A to 6C are views respectively showing states where the related-art pulse photometry probe is wound around bars 70 of 6φ, 8φ, and 10φ, as viewed from the end face direction, and FIGS. 7A to 7C are views respectively showing states where the pulse photometry probe 10 is wound around bars 70 of 6φ, 8φ, and 10φ, as viewed from the end face direction. In the embodiment of the invention, as shown in FIG. 4, the light emitter 21 and the light receiver 22 have a vertically elongated rectangular shape in a plan view. In the related-art pulse photometry probe, the light emitter and the light receiver have a laterally elongated rectangular shape in a plan view. Also because of the influence of this configuration, the probe is divide into a block B1 which includes the light emitter, a block B2 which includes the cable connecting the light emitter with the light receiver, and a block B3 which includes the light receiver, and exhibits a state where the bars 70 are surrounded by respective triangles and apertures are formed. When disturbance light enters through the apertures and is detected by the light receiver, there may occur a situation where a false measurement is caused.

On the other hand, in the pulse photometry probe 10 of the embodiment of the invention, because the light emitter 21 and the light receiver 22 have a vertically elongated rectangular shape in a plan view as shown in FIG. 4, the slits 31 of the cover sheet 30 have a function of allowing the probe to be finely bent, and the second lead wire 24 has the slack portion F which attains the adequate length extending from the basal portion 26 to the light receiver 22, the pulse photometry probe 10 is properly wound around the respective bars 70 as shown in FIGS. 7A to 7C. Therefore, it is possible to prevent a situation where apertures are formed, from occurring, and a false measurement due to disturbance light entering through apertures can be prevented from being caused.

Figure 8:
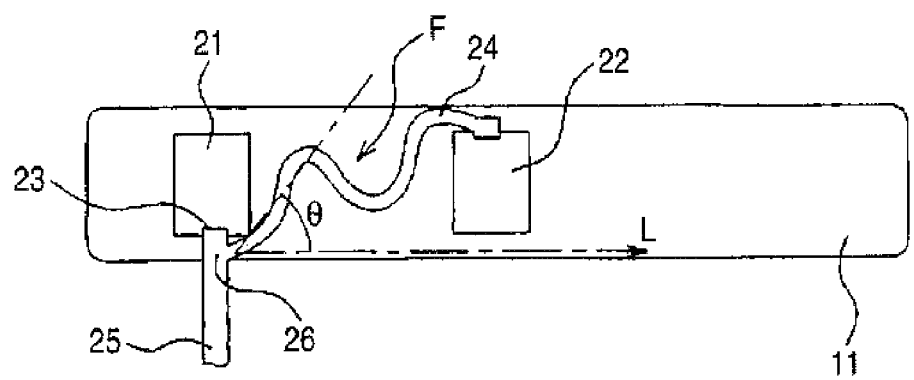
FIG. 8 is a plan view showing a configuration where the second lead wire of FIG. 4 is changed.

The embodiment has the configuration where the first lead wire 23 and the second lead wire 24 are connected from the same side to the light emitter 21 and the light receiver 22. Alternatively, another configuration may be employed where, as shown in FIG. 8, the first lead wire 23 is connected to the light emitter 21 from the lower side of FIG. 8, and the second lead wire 24 is connected to the light receiver 22 from the upper side of FIG. 8. Also in this configuration, the second lead wire 24 has the slack portion F which attains the adequate length extending from the basal portion 26 to the light receiver 22. Moreover, the second lead wire 24 extends toward the light receiver 22 at the angle θ which is 30 degrees or more from the basal portion 26, with respect to the distance direction L of the light emitter 21 and the light receiver 22.

Figure 9:
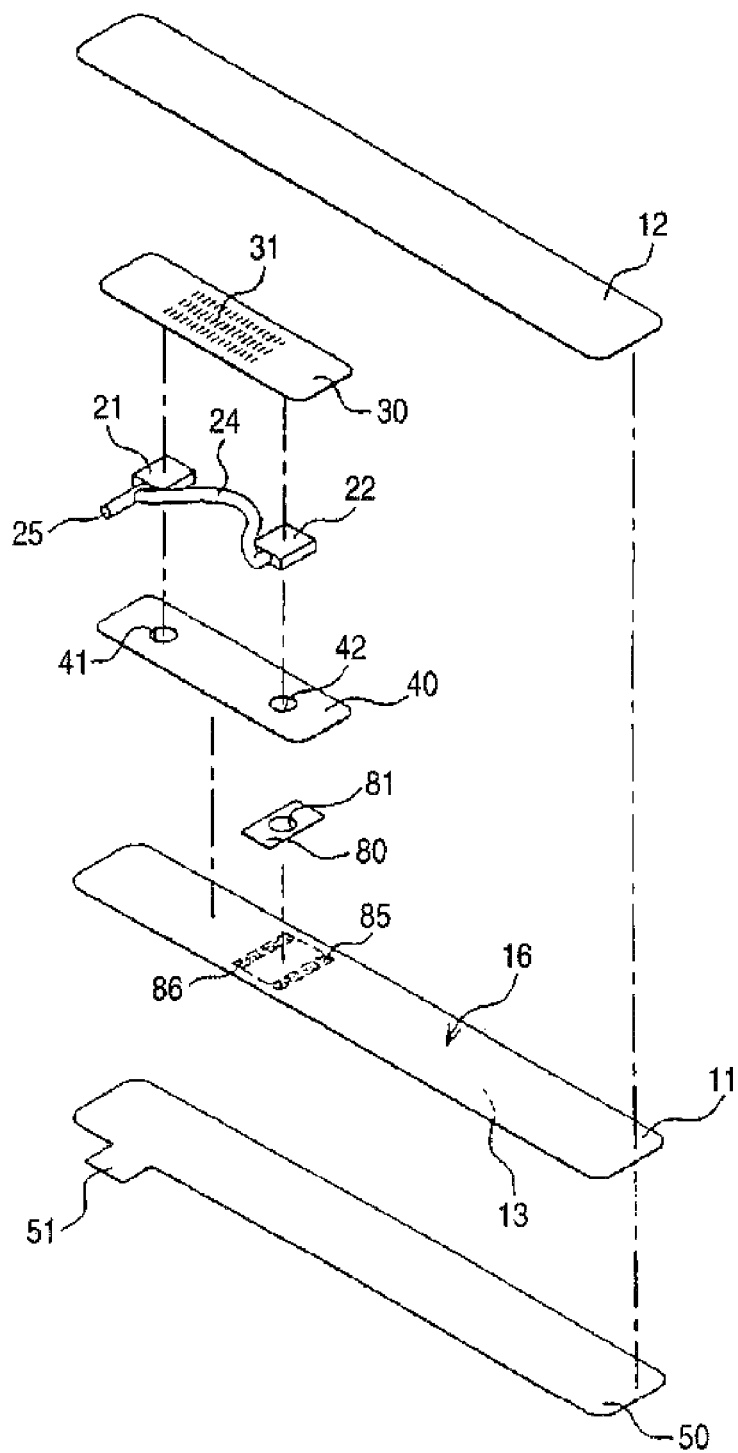
FIG. 9 is an assembly perspective view of an embodiment of the pulse photometry probe in which the configuration of a light intensity adjuster in the embodiment of FIG. 1A is changed.

The light intensity adjuster 15 is configured by printing in, for example, blue. Alternatively, as shown in FIG. 9, the light intensity adjuster may be configured by a blue narrow plate 80 in which a hole 81 is opened, and blue printed portions 85, 86 provided in the second sheet 11. In this configuration, when the plate 80 is placed on a region of the second sheet 11 corresponding to the light-receiving side face of the light receiver 22, the blue printed portions 8b, 86 are located on the both sides of the plate 80, and the position and area of the region formed by the plate 80 and the blue printed portions 85, 86 are equal to those of the light intensity adjuster is of FIG. 1A.

Also in the configuration of FIG. 9, the plate 80 included in the light intensity adjuster is narrow, the blue printed portions 85, 86 are provided in the second sheet 11, and the probe is properly wound around a living body without substantially producing a flat plate-like portion which, when the probe is attached to a living body, is formed by a hardly bendable portion. Therefore, a situation where apertures are formed can be prevented from occurring.

According to an aspect of the invention, in the cover sheet 30 which protects the light emitter 21 and the light receiver 22, the slits 31 that enable the cover sheet 30 to be elastic in the distance direction of the light emitter 21 and the light receiver 22 are formed. When the pulse photometry probe is attached to a living body, therefore, the cover sheet 30 is extended to enable the pulse photometry probe to be attached to a finger or the like without forming apertures. The pulse photometry probe includes the second lead wire 24 having the slack portion which attains an adequate length extending from the basal portion 26 that is bundled with the first lead wire 23, to the light receiver 22. When the pulse photometry probe is attached to a living body, therefore, the second lead wire 24 has an adequate length to obtain a state where the wire extends from the basal portion 26 to the light receiver 22, whereby, when attached to a living body, the light receiver 22 can be prevented from being pulled by the second lead wire 24, and the pulse photometry probe can be attached to a finger or the like without forming apertures.

According to an aspect of the invention, the light intensity adjuster is disposed in the second sheet 11 corresponding to the light-receiving side face of the light receiver 22. Therefore, the light intensity adjuster functioning as the second sheet 11 is property attached to a living body such as a finger without forming apertures as compared with the case where the light intensity adjuster is formed by a hard plate.

In the case where the pulse photometry probe is to be attached to a neonatal infant or the like who has delicate skin and a thin attached portion, particularly, the easy attachment can reduce the required force to a minimum level, and apertures are hardly formed, thereby making it easier for the light emitter 21 and the light receiver 22 to be opposed with each other. Therefore, the measurement accuracy is not impaired. The contact area between the attached portion and the pulse photometry probe is increased, and hence there is a further advantage that slippage or disengagement in the case of body motion can be prevented from occurring.

What is claimed is:

1. A pulse photometry probe comprising:
   a light emitter having a first face from which light is emitted toward a living body;

a light receiver having a second face which receives the light from the living body;

a surface sheet which faces the first face of the light emitter and the second face of the light receiver;

a cover sheet in which at least one slit is formed, the light emitter and the light receiver which are disposed between the surface sheet and the cover sheet; and a lead wire which includes:
- a first lead wire connected to one of the light emitter and the light receiver;
- a second lead wire connected to the other one of the light emitter and the light receiver; and
- a basal portion at which the first lead wire and the second lead wire are bundled, wherein the second lead wire includes at least one slack portion between the basal portion and the other one of the light emitter and the light receiver, wherein the pulse photometry probe is configured to circumferentially wrap around an axis extending from a proximal end to a distal end of an appendage and, wherein the at least one slit is configured to reduce aperture formation and thereby reduce interference from ambient light when the pulse photometry probe is wrapped around the axis extending from the proximal end to the distal end of the appendage.

2. The pulse photometry probe according to claim 1, further comprising a first sheet which covers the surface sheet and the cover sheet.

3. The pulse photometry probe according to claim 2, wherein the basal portion is covered by at least one of the cover sheet and the first sheet.

4. The pulse photometry probe according to claim 1, wherein the slit passes through the cover sheet.

5. The pulse photometry probe according to claim 1, wherein the slit has a bottom portion on the cover sheet without passing through the cover sheet.

6. The pulse photometry probe according to claim 1, wherein the second lead wire extends toward the other one of the light emitter and the light receiver at an angle, which is 30 degrees or more, from the basal portion, with respect to a direction in which the light emitter and the light receiver are arranged.

7. The pulse photometry probe according to claim 1, wherein a light intensity adjuster is disposed on a portion of the surface sheet, and the portion of the surface sheet faces the second face of the light receiver.

8. The pulse photometry probe according to claim 1, further comprising a second sheet to be in contact with the living body, wherein the surface sheet includes a third face which faces the light emitter and the light receiver and a fourth face opposite to the third face, and the second sheet faces the fourth face of the surface sheet.

9. The pulse photometry probe according to claim 8, wherein a light intensity adjuster is disposed in a portion of the second sheet, and the portion of the second sheet faces the second face of the light receiver.

10. The pulse photometry probe according to claim 1, wherein the slit enables the cover sheet to be elastic in a direction in which the light emitter and the light receiver are arranged.

11. The pulse photometry probe according to claim 1, wherein the cover sheet protects the light emitter and the light receiver.

12. The pulse photometry probe according to claim 1, wherein the slack portion attains an adequate length of the second lead wire, when the pulse photometry probe is attached to the living body.

13. The pulse photometry probe according to claim 1, wherein the slit extends in a direction perpendicular to a longitudinal direction of the cover sheet.

14. The pulse photometry probe according to claim 1, wherein the slit is disposed between a first portion of the cover sheet facing the light emitter and a second portion of the cover sheet facing the light receiver.

15. The pulse photometry probe according to claim 1, wherein a plurality of the slits are formed in the cover sheet.

16. The pulse photometry probe according to claim 1, wherein the slack portion has a shape including at least one bent portion.

17. The pulse photometry probe according to claim 1, wherein the at least one slit is formed in a portion between the light emitter and the light receiver.

18. The pulse photometry probe according to claim 1, wherein the appendage is one of a finger and a toe.

* * * * *